United States Patent [19]

Ohkuma et al.

[11] Patent Number: 5,541,181
[45] Date of Patent: Jul. 30, 1996

[54] COMPOUND PRODUCED BY A STRAIN OF MICROMONOSPORA

[75] Inventors: Hiroaki Ohkuma, Itabashi-ku; Seikichi Kobaru, Funabashi, both of Japan

[73] Assignee: Bristol-Myers Squibb Company, Princeton, N.J.

[21] Appl. No.: 249,518

[22] Filed: May 26, 1994

[51] Int. Cl.$^6$ .................... C07D 243/10; A61K 31/55
[52] U.S. Cl. .................. 514/220; 435/252.1; 435/117; 540/495
[58] Field of Search .................. 514/220; 540/495

[56] References Cited

U.S. PATENT DOCUMENTS 4,663,347  5/1987  Atkinson et al. .................... 514/467

FOREIGN PATENT DOCUMENTS 3232887  2/1990  Japan.

OTHER PUBLICATIONS

Stephen M. Berge et al., Journal of Pharmaceutical Sciences, "Pharmaceutical Salts", vol. 66, No. 1, pp. 1–19, 1977.
Bengt Samuelsson, Science, "Leukotrienes: Mediators of Immediate Hypersensitivity Reactions and Inflammation", vol. 220, pp. 568–575, 1983.
J. Orskov, Investigations Into The Morphology of the Ray Fungi, Levin& Munksgaard Publishers, pp. 9–12. 1973.
Derek J. Hook et al., the Journal of Antibiotics, "Identification of the Inhibitory Activity of Carbazomycins B and C Against 5-Lipoxygenase, a A New Activity for These Compounds", vol. XLII, No. 10, pp. 1347–1348, 1990.
The Actinomyceted, vol. II, pp. 328–335. (1957).
E. B. Shirling et al., International Journal of Systematic Bacteriology, "Methods for Characterization of Streptomyces Species", vol. 16, No. 3, pp. 313–340, 1966.
Tadashi Arai., Culture Media for Actinomycetes, "The Society for Actinomycetes", pp. 1–31, 1975.
H. A. Lechevalier et al., A Critical Evaluation of the Genera of Aerobic Actinommycetes, pp. 393–405. 1969.
Joseph L. Staneck et al., Applied Microbiology, "Simplified Approach to Identification of Aerobic Actinomycetes by Thin–Layer Chromatography", vol. 28, No. 2, pp. 226–231, 1974.
Mary P. Lechevalier et al., Biochemical Systematics and Ecology, "Chemotaxonomy of Aerobic Actinomycetes: Phospholipid Composition", vol. 5, pp. 249–260, 1977.
D. E. Minnikin et al., Journal of General Microbiology, "Differentiation of Mycobacterium, Nocardia, and Related Taxa by Thin–Layer Chromatographic Analysis of Whole–Organism Mehtanolysates", vol. 88, pp. 200–204, 1975.
M. D. Collins et al., Journal of Applied Bacteriology, "A Note on the Separation of Natural Mixtures of Bacterial Menquinones Using Reverse Phase Thin–Layer Chromatography", vol. 48, pp. 277–282, 1980.
Ken–Ichiro Suzuki et al., International Journal of Systematic Bacteriology, "Taxonomic Significance of Cellular Fatty Acid Composition in Some Coryneform Bacteria", vol. 33, No. 2, pp. 188–200, 1983.
Anderson Maxwell et al., Journal of Natural Products, "Novel Prenylated Hydroxybenzoic Acid Derivatives From Piper Saltuum", vol. 52, No. 3, pp. 614–618, 1989.
Problems in the Classification of Antagonistic Actinomycetes, published by The American Institute of Biological Sciences, pp. 1–165, 1957.
Anderson Maxwell et al., Journal of Natural Products, "Prenylated 4–Hydroxybenzoic Acid Derivatives From Piper Marginatum", vol. 51, No. 2, pp. 370–373, 1988.
Kazuo Shin–ya et al., Tetrahedron Letters, "The Structure of Benthocyanin A. An New Free Radical Scavenger of Microbial Origin", vol. 32, No. 7, pp. 943–946, 1991.

*Primary Examiner*—Mark L. Berch
*Attorney, Agent, or Firm*—Thomas R. Savitsky

[57] ABSTRACT

Disclosed is the novel compound BU-4664L and derivatives thereof. The compound is produced by fermentation of *Micromonospora* sp. M990-6. The compound possesses anti-inflammatory and/or anti-tumor cell activities. BU-4664L has the following structure:

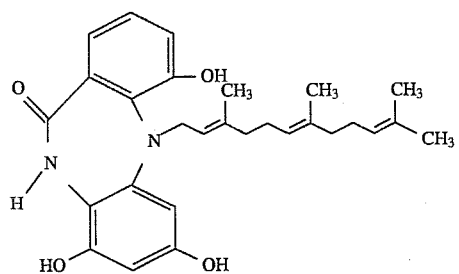

2 Claims, 3 Drawing Sheets

COMPOUND PRODUCED BY A STRAIN OF MICROMONOSPORA

FIELD OF THE INVENTION

The present invention concerns a novel compound and derivatives thereof produced by a strain of *Micromonospora*.

BACKGROUND OF THE INVENTION

The present invention concerns a novel compound produced by a strain of *Micromonospora*. The novel compound is useful as an inhibitor of the mammalian 5-lipoxygenase enzyme system. The 5-lipoxygenase enzyme controls the biosynthesis of the leukotriene class of compounds. Inhibitors of 5-lipoxygenase prevents or diminishes the adverse effects of the leukotrienes in a mammalian subject (see for example, U.S. Pat. No. 4,663,347, incorporated herein by reference in its entirety). Leukotrienes are important mediators of inflammatory diseases through their ability to modulate leukocyte and lymphocyte functions (see, B. Samuelsson, *Science*, 220, 568 (1983)). Thus, the novel compound of the invention is effective in controlling disease states of a mammalian subject relative to the 5-lipoxygenase system and/or the synthesis leukotrienes.

It has also been found that the novel fermentation compound of the invention and certain alkylated and acylated derivatives thereof as hereinafter described possess anti-tumor cell activity.

SUMMARY OF THE INVENTION

The present invention is based on the discovery of a new microorganism strain which produces a biologically active compound. The compound of the invention is referred to herein as compound "BU-4664L" which term also includes pharmaceutically acceptable salts of the compound. The invention also includes certain derivatives of compound BU-4664L. Thus, the present invention is directed to a compound of the formula

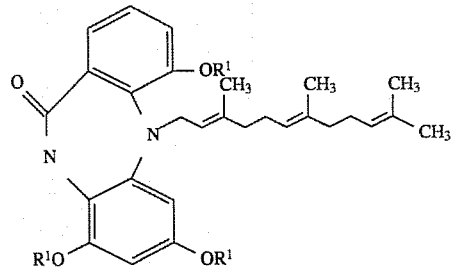

(A)

wherein each $R^1$ is, independently, H, a $C_1$–$C_6$ alkyl group, or a $C_2$–$C_7$ acyl group; or a pharmaceutically acceptable salt thereof. The present invention is also directed to pharmaceutical compositions comprising one or more of the compounds of the invention together with a pharmaceutically acceptable carrier.

Compound BU-4664L has been found to be produced by a microorganism, strain M990-6, identified as being a species of *Micromonospora*. Thus, the present invention is also directed to a biologically pure culture of *Micromonospora* sp. M990-6. It is also contemplated that mutants and variants of *Micromonospora* sp. M990-6 are also within the scope of the present invention, whether created by conventional physical or chemical means or by recombinant genetic engineering techniques. The present invention also includes a process for producing the compounds of the invention comprising cultivating under aerobic conditions *Micromonospora* sp. M990-6 or a mutant or variant thereof in a suitable culture medium containing a carbon source and a nitrogen source at a pH and temperature and for a time sufficient for production of compound BU-4664L.

Additionally, the present invention is directed to a method for treating pulmonary conditions, inflammation, cardiovascular conditions, or skin conditions which comprises administering to a patient in need of treatment an effective amount of compound BU-4664L.

Furthermore, the present invention is directed to a method for inhibiting mammalian tumor cells, particularly melanoma and leukemia cells, comprising contacting said cells with an effective amount of the compound of Formula A.

DETAILED DESCRIPTION OF THE INVENTION

Figure 1:
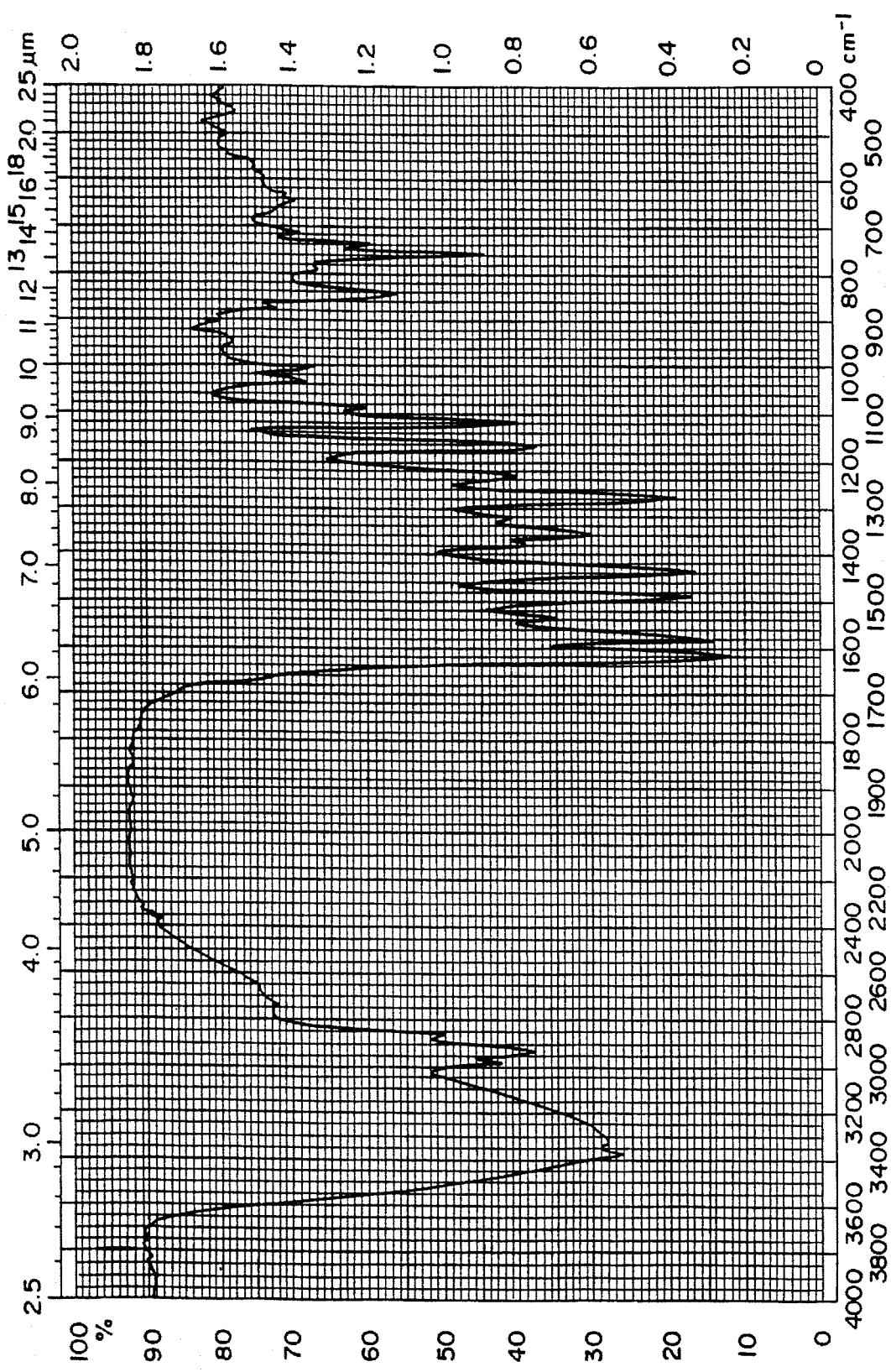
FIG. 1—Infrared (IR) spectrum of compound BU-4664L (KBr).

An actinomycete, strain M990-6, which produces the novel biologically active compound, BU-4664L, was isolated from a soil sample collected in Colombo, Sri Lanka. Based on the morphological, cultural and physiological characteristics and cell chemistry, strain M990-6 was identified as *Micromonospora* sp. This organism was deposited on Nov. 17, 1992, with the American Type Culture Collection (ATCC), 12301 Parklawn Drive, Rockville, Md. 20852, U.S.A., under the Accession Number ATCC-55378.

It is to be understood that the present invention is not limited to use of the particular strain M990-6 or to organisms fully answering the description contained herein. It is especially intended to include other BU-4664L producing strains or mutants or variants of said organisms which can be produced from the described organism by known means such as X-ray irradiation, ultraviolet irradiation, treatment with nitrogen mustard, phage exposure, and the like; or through the use of recombinant genetic engineering techniques.

Compound BU-4664L is produced by cultivating *Micromonospora* sp. M990-6, or a mutant or a variant thereof, in a conventional aqueous medium. The organism is grown in a nutrient medium containing known nutritional sources for acetinomycetes, i.e. assimilable sources of carbon and nitrogen plus optional inorganic salts and other known growth factors. Submerged aerobic conditions are preferably employed for the production of large quantities of active compounds, although for production of limited amounts, surface cultures and bottles may also be used. The general procedures used for the cultivation of other actinomycetes are applicable to the present invention. The nutrient medium should contain an appropriate assimilable carbon source such as sucrose, starch, glucose, xylose, fructose, glycerol, L-arabinose, galactose, mannose, lactose, cellobiose, melibiose, trehalose, or raffinose. As nitrogen sources, ammonium chloride, ammonium sulfate, urea, ammonium nitrate, sodium nitrate, etc. may be used or organic nitrogen sources such as peptone, fish meat extract or fish meal, yeast extract, meat extract such as beef extract, corn steep liquor, soybean powder, NZ-case, cotton seed flour, etc., may be used, or any combination thereof. There may also be added if necessary nutrient inorganic salts to provide sources of sodium, potassium, calcium, ammonium, phosphate, sulfate, chloride, bromide, carbonate, zinc, magnesium, manganese, cobalt, iron and the like. Ordinarily, optimum production of the compounds of the invention is obtained in shake flasks after an appropriate incubation period. Aeration in shake flasks is achieved by agitation, e.g., shaking on a rotary shaker. If fermentation is to be carried out in tank fermentors, it is desirable to produce a vegetative inoculum in a nutrient broth by inoculating the broth culture from a slant culture of a lyophilized culture of the organism or with vegetative mycelia stored at a low temperature (e.g. −80° C.) in the presence of glycerol. After obtaining an active inoculum in this manner, it is aseptically transferred to the fermentation tank medium. Agitation in the tank fermentor is provided by stirring and aeration may be achieved by injection of air or oxygen into the agitated mixture. Production of BU-4664L may be monitored using chromatographic or spectroscopic techniques, or by a conventional biological assay.

Preferred culture conditions include a pH of about 6 to about 9 and temperature of about 16° C. to about 45° C., and an incubation period of about 2 days to about 20 days. More preferred conditions include a pH of about 7, a temperature of about 24° C. to about 36° C., and an incubation period of about 3 days to about 15 days.

After cultivation and production of compound BU-4664L, said compound can be isolated by techniques known in the art and/or taught herein. For example, the fermented whole broth can be extracted by contact with a suitable organic solvent such as n-butanol, n-butyl acetate or 4-methyl- 2-pentanone, preferably under agitation. The organic layer can then be separated, e.g., by centrifugation followed by removal of the solvent, e.g., by evaporation to dryness, preferably under vacuum. The resulting residue can then optionally be reconstituted (e.g., in water, ethyl acetate, methanol or a mixture thereof) and re-extracted with a suitable organic solvent such as hexane, carbon tetrachloride, methylene chloride or a mixture thereof. After removal of solvent, the active compound can be further purified/isolated by use of standard techniques such as chromatography, particularly column chromatography, optionally followed by further purification, e.g., by use of reverse phase chromatography. Various modifications to any particular isolation/purification procedure will be apparent to a skilled artisan. The activity can be monitored during purification by a biological assay and/or physico-chemical techniques such as thin layer chromatography (TLC).

Derivatives of compound BU-4664L are produced by reacting one or more of the hydroxyl groups of BU-4664L with a suitable reagent to form alkylated or acylated derivatives. Alkylation is accomplished by standard alkylating procedures known in the art, for example, methylation of compound BU-4664L with diazomethane in a benzene-methanol mixture. Acylation is accomplished by standard acylating procedures known in the art, for example, by reacting compound BU-4664L with a suitable $C_2$-$C_7$ carboxylic acid, such as acetic acid, under conditions to form the desired acylated derivative.

Preferred compounds of Formula A are wherein $R^1$ is H, a $C_1$-$C_3$ alkyl group or an acyl group of the formula

wherein $R^2$ is phenyl or a $C_1$-$C_3$ alkyl group. The term "alkyl" includes both straight chain and branched alkyl groups. More preferred compounds of Formula A are wherein each $R^1$ is methyl or wherein each $R^1$ is acetyl. The most preferred compound of Formula A is compound BU-4664L (i.e., wherein $R^1$ is H).

For medicinal use, the pharmaceutically acceptable acid addition salts, those salts in which the anion does not contribute significantly to toxicity or pharmacological activity of their organic cation, are preferred. The acid addition salts are obtained either by reaction of one or both active compounds with an organic or inorganic acid, preferably by contact in solution, or by any of the standard methods detailed in the literature and available to a practitioner skilled in the art. Pharmaceutically acceptable salts of the compounds of the invention are illustratively hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane and ethanesulfonic, hydroxymethane- and hydroxyethane-sulfonic. (See, for example, "Pharmaceutical Salts," *J. Pharm. Sci.* 66(1):1–19 (1977)).

The compounds of the invention (i.e., of Formula A) possess anti-tumor cell activity. The compounds are effective against mammalian tumor cells, preferably against human tumor cells such as leukemia cells, melanoma cells, colorectal carcinoma cells and colon carcinoma cells. The anti-tumor cell method of the invention results in inhibition of tumor cells. The term "inhibition" when used in conjunction with the anti-tumor method refers to suppression, killing, stasis, or destruction of tumor cells. The anti-tumor method preferably results in prevention, reduction or elimination of invasive activity and related metastasis of tumor cells. The term "effective amount" when used in conjunction with the anti-tumor cell method refers to the amount of the compound(s) sufficient to result in inhibition of mammalian tumor cells.

For the anti-tumor method of the invention, a typical effective unit dose of the compounds given orally or parenterally would be from about 5 to about 100 mg/kg of body weight of the subject with a daily dose ranging from about 15 to about 300 mg/kg of body weight of the subject.

The present invention also provides a method of treatment of disease states, in particular inflammation, caused by the 5-lipoxygenase system and/or by the synthesis of the Leukotrienes $C_4$, $D_4$, $E_4$ and $F_4$ as well as Leukotriene $B_4$ in mammals especially in a human subject. This method comprises administering to said subject an effective amount of compound BU-4664L. Compound BU-4664L may be used to treat or prevent mammalian (especially human) disease states such as pulmonary conditions, inflammation, cardiovascular conditions, or skin conditions. More specific disease states include erosive gastritis; erosive esophagitis; inflammatory bowel disease; ethanol-induced hemorrhagic erosions; hepatic ischemia; noxious agent induced damage or necrosis of hepatic., pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage, trauma- or stress-induced cell damage; and glycerol-induced renal failure.

For the method of the invention related to the 5-lipoxygenase system and/or the biosynthesis of leukotriene, a typical effective unit dose of compound BU-4664L given orally or parenterally would be from about 5 to about 100 mg/kg of body weight of the subject with a daily dose ranging from about 15 to about 300 mg/kg of body weight of the subject.

For preparing pharmaceutical compositions from the compound(s) of this invention, inert, pharmaceutically acceptable carriers can be either solid or liquid. Solid form preparations include powders, tablets, dispersible granules, capsules, cachets, and suppositories.

In the pharmaceutical compositions of the invention the amount of active compound(s) of the invention is typically about 5 to about 95 weight percent of the total composition, preferably about 10 to about 80 weight percent.

A solid carrier can be one or more substances which may also act is diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound(s) is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool solidly.

Powders and tablets preferably contain between about 5 percent to about 95 percent by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

For topical administration, the compound(s) may be incorporated into lotions, ointments, gels, creams, salves, tinctures, and the like.

Tablets, powders, cachets, and capsules can be used as solid dosage forms suitable for oral administration.

Liquid form preparations include solutions suitable for oral or parenteral administration; suspensions, or emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions for injection or infusion may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound(s) in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules and powders in vials or ampoules. The unit dosage form can also be capsule, cachet, or tablet itself, or it can be the appropriate number of any of these packaged forms.

The following examples are to illustrate the invention but should not be interpreted as a limitation thereon. All percentages are by weight unless otherwise indicated.

EXAMPLE 1

BU-4664L, A New 5-Lipoxygenase Inhibitor
Taxonomy of the Producing Organism and
Production of BU-4664L Strain M990-6 (ATCC 55378) which produces a new 5-lipoxygenase inhibitory activity was identified as *Micromonospora* sp. This strain was isolated from a soil sample collected in Colombo, Sri Lanka.

Taxonomy of Strain M990-6

Cultural and physiological studies were done by using the media described by Shirling and Gottlieb (Shirling, E. B. and D. Gottlieb, "Methods for Characterization of *Streptomyces* Species," *Intern. J. Syst. Bact.*, 16:313–340, 1966), Waksman (Waksman, S. A., In The Actinomycetes. Vol. II. Classification, Identification and Description of Genera and Species, pages 328–334, The Williams & Wilkins Co., Baltimore, Md., 1961), Arai (Arai, T., In Culture Media for Actinomycetes. The Society for Actinomycetes, Japan, 1975), and Gauze (Gauze, G. F., et al., "Problems in the Classification of Antagonistic Actinomycetes," State Publishing House for Medical Literature (in Russian), Medzig, Moscow, 1957). Morphological and cultural characteristics were observed after incubation at 28° C. for three weeks according to the procedures recommended by Shirling and Gottlieb (Shirling, E. B. and D. Gottlieb, "Methods for Characterization of *Streptomyces* Species," *Intern. J. Syst. Bact.*, 16:313–340, 1966). Color names and hue numbers are given according to the Manual of Color Names (Japan Color Enterprise Co., Ltd., 1987). Utilization of carbohydrates and other physiological tests were carried out by the methods described by Shirling and Gottlieb (Shirling, E. B. and D. Gottlieb, "Methods for Characterization of *Streptomyces* Species," *Intern. J. Syst. Bact.*, 16:313–340, 1966) and Waksman (Waksman, S. A., In The Actinomycetes. Vol. II. Classification, Identification and Description of Genera and Species, pages 328–334, The Williams & Wilkins Co., Baltimore, Md., 1961). Temperature range for growth was determined on yeast starch agar (Arai, T., In Culture Media for Actinomycetes. The Society for Actinomycetes, Japan, 1975) using a temperature gradient incubator TN-3 (Toyo Kagaku Sangyo Co., Ltd.).

Biomass for the chemotaxonomic analysis were prepared by using lyophilized whole cells grown at 28° C. for four days with a rotary shaker in a liquid medium (glucose 1% and yeast extract 1%, pH 7.0). Cell wall analysis was performed by the methods of Lechevalier and lechevalier (Lechevalier, H. A. and M. P. Lechevalier, "A Critical Evaluation of the Genera of Aerobic Actinomycetes," In The Actinomycetales, H. Prauser, editor, pages 393–405, Jena, Gustav Fischer Verlag, 1970) as modified by Staneck and Roberts (Staneck, J. L. and G. D. Roberts, "Simplified Approach to Identification of Aerobic Actinomycetes by Thin-layer Chromatography," *Appl. Microbiol.*, 28:226–231, 1974). Phospholipid and mycolate composition were determined after Lechevalier (Lechevalier, M. P., et al., "Chemotaxonomy of Aerobic Actinomycetes: Phospholipid Composition," *Biochem. Syst. Ecol.*, 5:249–260, 1977) and Minnikin, et al. (Minnikin, D. E., et al., "Differentiation of

*Mycobacterium, Norcardia* and Related Taxa by Thin-layer Chromatographic Analysis of Whole-Organism Methanolysates," *J. Gen. Microbiol.* 88:200–204, 1975), respectively. Menaquinone was analyzed by the procedure of Collins, et al. (Collins, et al., "A Note on the Separation of natural Mixtures of Bacterial Menaquinones Using Reverse-phase Thin-layer Chromatography," *J. Appl. Bacteriol.*, 48:277–282, 1980). Fatty acid was determined by the method of Suzuki, et al. (Suzuki, K. and K. Komagata, "Taxonomic Significance of Cellular Fatty Acid Composition in Some Coryneform Bacteria," *Int. J. Syst. Bacteriol.*, 33:188–200, 1983).

Morphology and Cultural Characteristics

Strain M990-6 grew better on organic media than synthetic media. On organic agar media, vegetative mycelia raised, granulated and developed into the mycelium and did not fragment into short elements of form spores. At the top of a short sporophore it bore a single brownish olive spore which, at maturity, is oval (0.8×0.8 µ) in shape. spore-surface showed a warty-like structure. Rudimentary and retarded aerial mycelia were formed on sucrose nitrate agar, nutrient agar and Gauze's I agar (Gauze, G. F., et al., "Problems in the Classification of Antagonistic Actinomycetes," State Publishing House for Medical Literature (in Russian), Medzig, Moscow, 1957), but no sporulating aerial mycelium was observed.

The color of vegetative mycelia and reverse side colon ranged from bright orange to brownish olive or black. No diffusible pigment was produced. The macroscopic properties of strain M990-6 on various agar media are summarized in Table 1.

Physiological Characteristics

The physiological characteristics and the utilization of carbon sources are shown in Tables 2 and 3, respectively.

TABLE 2

| Physiological Characteristics of Strain M990-6 | |
|---|---|
| Test | Results |
| Starch hydrolysis (On ISP med. No. 4) | Positive |
| Nitrate reduction (Difco, nitrate broth) | Positive |
| Milk (Difco, 10% skimmed milk) | |
| Coagulation | Positive |
| Peptonization | Positive |
| Cellulose decomposition | Negative |
| (sucrose nitrate solution with a paper strip as the sole carbon source) | |
| Gelatin liquefaction | |
| On plain gelatin | Positive |
| On glucose peptone gelatin | Positive |
| Melanin formation (On ISP med. No. 7) | Negative |
| Temperature range for growth (°C.) | 16–45 |
| Optimum temperature (°C.) | 24–36 |
| (On yeast starch agar) | |
| pH range for growth | 6–9 |
| Optimum pH | 7 |
| (On trypticase soy broth, BBL) | |

TABLE 1

| Cultural characteristics of strain M990-6 | | | | |
|---|---|---|---|---|
| Medium | Vegetative mycelium | Reverse Side | Aerial Mycelium | Diffusible Pigment |
| Sucrose nitrate agar (Waksman med. 1) | Bright orange (68) | Bright Orange (68) | White (388), Powdery, Thin | None |
| Glycerol nitrate agar | Brownish olive (163) | Brownish olive (163) | None | None |
| Glucose asparagine agar (Waksman med. 2) | Bright orange (68) ~ dark grayish olive (172) | Bright orange (68) ~ dark grayish olive (172) | None | None |
| Yeast extract-malt extract agar (ISP med. 2) | Black (426) | Black (426) | None | None |
| Oatmeal agar (ISP med. 3) | Bright orange (68) ~ yellowish brown (99) | Bright orange (68) ~ yellowish brown (99) | None | None |
| Inorganic salts-starch agar (ISP med. 4) | Strong yellowish orange (77) ~ brownish olive (163) | Strong yellowish orange (77) ~ brownish olive (163) | None | None |
| Glycerol asparagine agar (ISP med. 5) | Brownish olive (163) | Brownish olive (163) | None | None |
| Tyrosine agar (ISP med. 7) | Brownish olive (163) | Brownish olive (163) | None | None |
| Nutrient agar (Waksman med. 14) | Brownish olive (163) | Brownish olive (163) | White (388) Powdery, Scant | None |
| Yeast starch agar | Black (426) | Black (426) | None | None |
| Gauze's agar | Strong yellowish orange (77) | Strong yellowish orange (77) | White (388), Powdery, Scant | None None |
| Oatmeal-yeast extract agar | Bright orange (68) ~ brownish olive (163) | Bright orange (68) ~ brownish olive (163) | None | None |
| Bennett's agar (Waksman med. 30) | Black (426) | Black (426) | None | None |

TABLE 3

Utilization of Carbon Sources by Strain M990-6

| Carbon Source | Growth |
| --- | --- |
| D-Glucose | + |
| L-Arabinose | + |
| D-Xylose | + |
| Inositol | − |
| Mannitol | − |
| D-Fructose | + |
| L-Rhamnose | − |
| Sucrose | + |
| Raffinose | + |

−: Negative,
+: Positive
(ISP med. No. 9, 28° C. for 21 days)

Cell Chemistry

Analysis of hydrolyzed whole cells indicated the presence of meso-diaminopimelic acid with no LL isomer present. Sugar analysis of hydrolyzed whole cells indicated the presence of glucose, galactose, arabinose, xylose and ribose. This represents a type II and a type D sugar pattern. Mycolic acids were not detected. By phospholipids analysis, the wall had a type PII containing phosphatydilethanolamine, phosphatydilinositol and phosphatydilinositol mannoside. Analysis of the menaquinone composition revealed 35% MK-10($H_4$), 22% MK-9($H_4$), 14% MK-10($H_6$), 10% MK-9($H_6$), 6% MK-10($H_2$), 6% MK-10($H_8$), 4% MK-9($H_8$) and 3% MK-9($H_3$). The cellular fatty acids composition was shown in Table 4.

TABLE 4

Fatty Acid Composition of Strain M990-6

| Fatty Acid Composition (%) | | | | | | | | | | | | | | |
| --- | --- | --- | --- | --- | --- | --- | --- | --- | --- | --- | --- | --- | --- | --- |
| Straight Chain | | | | | Branched Chain | | | | | Unsaturated Chain | | | | |
| 15:0 | 16:0 | 17:0 | 18:0 | 19.0 | i-15 | i-16 | i-17 | a-15 | a-17 | i-17:1 | i-18:1$^9$ | 10Me16 | 10Me17 | 10Me18 |
| 1 | 1 | 6 | 2 | 1 | 20 | 8 | 13 | 5 | 25 | 7 | 4 | 1 | 3 | 1 |

The taxonomic results of this strain described above coincided with the characteristics of the genus Micromonospora Orskov 1923. Thus, it is concluded that the culture M990-6 represents a species of *Micromonospora*.

Strain M990-6 was deposited with the American Type Culture Collection (ATCC), 12301 Parklawn Drive, Rockville, Md., 20852, U.S.A. on Nov. 17, 1992, under the provisions of the Budapest Treaty, under Access Number ATCC 55378.

Fermentation

Stocked Culture. Strain M990-6 was propagated on Bn-2 agar slant composed of soluble starch (Nichiden Kagaku Co.) 0.5%, glucose 0.5%, meat extract (Mikuni Chemical Industries Co., Ltd.) 0.1%, yeast extract (Oliental Yeast Co.) 0.1%, NZ-case (Humko Sheffield Chemical Co.) 0.2%, NaCl 0.2%, $CaCO_3$ 0.1% and agar (Junsei Chemical Co.) 1.6%, for 14 days at 32° C., a portion of the mature agar slant was inoculate into 100 ml of seed medium in a 500-ml Erlenmeyer flask and incubated for 4 days at 28° C. and 200 rpm on a rotary shaker. The vegetative medium was composed of soluble starch 2%, glucose 0.5%, NZ-case (Humco Sheffield Chemical Co.) 0.3%, yeast extract (Oriental Yeast Co.) 0.2%, fish meal D30X (Banyu Nutrient) 0.5% and $CaCO_3$ 0.3%.

20-Jar Fermentation. A 5-ml portion of the seed culture was transferred into a 500-ml Erlenmeyer flask containing 100 ml of the seed medium described above. Fermentation was carried out for 3 days at 28° C. and 200 rpm. This seed culture (500 ml) was inoculated into a 20-liter jar fermentor containing 12 liters of the production medium composed of soluble starch 2%, Pharmamedia (Trader's Protein) 1%, yeast extract 0.2%, $ZnSO_4 \cdot 7H_2O$ 0.003% and $CaCO_3$ 0.4% (pH 7.0) and fermented for 3 days under the following conditions: temperature, 28° C.; aeration, 10 liters/minute; internal pressure, 0.5 kg/$cm^2$; agitation, 250 rpm. For preparation of an assay sample, a 3-ml of the whole broth was extracted with the same volume of n-butanol. After centrifugation, the solvent layer was evaporated to dryness and dissolved into the same volume of 10% dimethylsulfoxide (DMSO) solution. The solution was used as an assay sample. The inhibitory activity of the sample against 5-lipoxygenase was shown 72% at 200 fold dilution after 3 days of jar fermentation.

EXAMPLE 2

BU-4664L, A New 5-Lipoxygenase Inhibitory and Antitumor Antibiotic Isolation, Characterization, Structure and Biological Activity Isolation and Purification The harvested broth (52 liters) was stirred with n-butanol (28 liters) for one hour. The organic extract (25 liters) was separated from the broth using a Sharples type centrifuge (Kokusan No. 4A) and concentrated to dryness in vacuo to afford a crude solid (55.6 g). This solid was successively partitioned between equal volumes (one liter of aqueous methanol, % adjusted to produce a biphase solution) and a solvent series of n-hexane (10.9 g), carbon tetrachloride (29.5 g) and methylene chloride (15.5 g). The methylene chloride partition fraction was dissolved with 40% aqueous methanol and applied on a column of Diaion HP-20 (4.0 i.d.×120 cm) which was developed successively with 0% and 80% aqueous methanol and 80% aqueous acetone. The eluates were collected in 20 ml fractions which were monitored by 5-lipoxygenase inhibitory assay and TLC ($SiO_2$, $CHCl_3$-MeOH-$H_2O$ 65:35:10, lower phase). The appropriate fractions were collected, concentrated in vacuo and chromatographed on a column of Sephadex LH-20 (10.0 i.d.×50 cm) using methylene chloride-methanol (1:1, v/v) as a developing solvent. After monitoring with TLC described above, the appropriate fractions were concentrated and applied to a silica gel column (Wako gel C-200, 3.0 i.d.×54 cm) using methylene chloride with an increasing amount of methanol (5–20%, v/v) as a developing solvent to afford a purified solid (318 mg). The solid was rechromatographed on a column of Sephadex LH-20 (4.0 i.d.×65 cm) with methylene chloride-methanol (4:6, v/v) elution to yield 241 mg of pure BU-4664L as a pale yellow amorphous solid.

Physico-chemical Properties

BU-4664L was obtained as a pale yellow amorphous powder. It is soluble in methanol, ethanol, ethyl acetate and dimethyl sulfoxide, slightly soluble in chloroform, but insoluble in n-hexane and water. It gave positive response to iodine vapor, sulfuric acid and ferric chloride, but negative to ninhydrin and anthrone tests. The FAB-MS (positive) spectrum of BU-4664L showed the pseudomolecular ions at m/z 462 (M+Na)$^+$ and 501 (M+K)$^+$ together with fragment ions at m/z 393, 325, 258 (base peak) and 69. The molecular formula of BU-4664L was established as $C_{28}H_{34}N_2O_4$ based on the microanalysis and FAB-MS spectra coupled with the $^1$H- and $^{13}$C-NMR spectral data (Tables 6 and 7). The physico-chemical data are summarized in Table 5.

TABLE 5

Physico-chemical Properties of BU-4664L

| Appearance | Pale yellow amorphous powder |
|---|---|
| Melting point | 184–185° C. |
| UV $\lambda_{max}$ nm($\epsilon$) | |
| in MeOH & 0.01N HCl—MeOH | 211 (65,800), 292(sh), |
| in 0.01N NaOH—MeOH | 208 (44,300), 252(sh), 280(sh), 340(sh), 553 (9,100) |
| IR $\nu_{KBr}$(cm$^{-1}$) | 3370, 2930, 1615, 1580, 1535, 1490, 1440, 1280, 1165, 1150 |
| Molecular formula | $C_{28}H_{34}N_2O_4$ |
| Microanalysis | $C_{28}H_{34}N_2O_4 \cdot \frac{1}{2}H_2O$ |
| | Calcd: Found: |
| | C  71.30%  71.59% |
| | H  7.49%  7.35% |
| | N  5.94%  5.91% |
| FAB-MS (m/z)(positive) | 462(M)$^+$, 485(M + Na)$^+$, 501(M + K)$^+$ |
| FAB-MS (m/z)(negative) | 461 (M − H)$^+$ |

TABLE 5-continued

Physico-chemical Properties of BU-4664L

| TLC, SiO$_2$ (Rf) (CHCl$_3$—MeOH—H$_2$O:65:35:10, lower phase) | 0.70 |
|---|---|

TABLE 6

$^1$H NMR Spectra of BU-4664L, Its Derivatives and Compound-I (400 MHz in DMSO-d$_6$)

| Proton | BU-4664L (1) | Triacetyl BU-4664L (2) | Trimethyl BU-4664L (3) | Compound-I (4) |
|---|---|---|---|---|
| 25-CH$_3$ | 1.51(3H, s) | 1.51(3H, s) | 1.51(3H, s) | |
| 24-CH$_3$ | 1.54(3H, s) | 1.53(3H, s) | 1.52(3H, s) | |
| 26-CH$_3$ | 1.61(3H, s) | 1.61(3H, s) | 1.61(3H, s) | |
| 23-CH$_3$ | 1.65(3H, s) | 1.63(3H, s) | 1.66(3H, s) | |
| 19-CH$_2$ | 1.19(2H, m) | | 1.87(2H, t, J=7.5) | |
| 15-CH$_2$ | | 1.87–1.97(8H, m) | | |
| 16-CH$_2$ | 1.97–2.03 (6H, m) | | 1.90–2.03(6H, m) | |
| 20-CH$_2$ | | | | |
| 12-CH$_2$ | 4.39(2H, d, J=6.0)* | 4.55(2H, d, J=8.8) | 4.51(2H, d, J=6.5) | |
| 17-H | 5.04(1H, qt, J=6.8 & 1.7) | 5.02(1H, m) | 4.99(1H, dd, J=6.8 & 1.3) | |
| 21-H | 5.06(1H, t, J=6.4) | 5.04(1H, m) | 5.03(1H, dd, J=6.8 & 1.3) | |
| 13-H | 5.25(1H, dd, J=6.0 & 0.9) | 5.18(1H, t, J=6.0) | 5.23(1H, t, J=6.0) | |
| 6-H | 6.15(1H, d, J=2.6) | 6.86(1H, d, J=2.6) | 6.46(1H, d, J=2.6) | 6.23(1H, d, J=2.6) |
| 8-H | 6.17(1H, d, J=2.6) | 7.08(1H, d, t=2.6) | 6.50(1H, d, J=2.6) | 6.37(1H, d, J=2.6) |
| 2-H | 6.70(1H, t, J=7.7) | 7.01(1H, t, J=8.1) | 6.90(1H, dd, J=8.1 & 7.7) | 6.84(1H, t, J=8.1) |
| 10-NH | 6.72(1H, s) | 7.30(1H, s) | 6.83(1H, s) | 6.86(1H, s) |
| 3-H | 6.83(1H, dd, J=7.7 & 1.7) | 7.50(1H, dd, J=8.1 & 1.7) | 7.13(1H, dd, J=8.1 & 1.3) | 7.07(1H, dd, J=8.1 & 1.3) |
| 1H | 7.06(1H, dd, J=7.7 & 1.7) | 7.18(1H, dd, J=8.1 & 1.7) | 7.22(1H, dd, J=7.7 & 1.3) | 7.28(1H, dd, J=8.1 & 1.3) |
| 7-OH | 9.03(1H, s) | | | |
| 9-OH | 9.94(1H, s) | | | |
| 4-OH | 10.03(1H, s) | | | |
| 9-COCH$_3$ | | 2.23(3H, s)** | | |
| 7-COCH$_3$ | | 2.39(3H, s)** | | |
| 4-COCH$_3$ | | 2.37(3H, s)** | | |
| 7-CH$_3$ | | | 3.68(3H, s) | 3.68(3H, s) |
| 9-CH$_3$ | | | 3.84(3H, s) | 3.84(3H, s) |
| 4-CH$_3$ | | | 3.88(3H, s) | 3.88(3H, s) |
| 5-NH | | | | 9.7791H, s) |

*Multiplicities and observed coupling constants in Hz are given in parentheses.
**Assignments may be interchanged.

TABLE 7

$^{13}$C NMR Spectral Data of BU-4664L (1), Its Trimethyl Derivative (3) and Compound-1 (4) (100 MHz in DMSO-d$_6$)

| Carbon | 1 | 3 | 4 |
|---|---|---|---|
| 1 | 122.2(d)$^b$ | 123.5(d) | 123.5(d) |
| 2 | 120.8(d) | 120.9(d) | 120.1(d) |
| 3 | 116.3(d) | 113.5(d) | 114.3(d) |
| 4 | 145.4(s) | 147.8(s) | 147.7(s) |
| 4a | 134.8(s)$^a$ | 134.4(s) | 139.6(s) |
| 5a | 134.5(s)$^a$ | 126.8(s) | 130.3(s) |
| 6 | 100.4(d) | 99.9(d) | 98.2(d) |
| 7 | 152.9(s) | 155.3(s) | 155.3(s) |
| 8 | 99.4(d) | 96.2(d) | 94.7(d) |
| 9 | 147.5(s) | 150.0(s) | 149.7(s) |
| 9a | 124.8(s) | 124.6(s) | 121.3(s) |
| 11-CONH | 167.5(s) | 167.1(s) | 167.6(s) |
| 11a | 141.1(s) | 141.3(s) | 122.5(s) |
| 12 | 47.4(t) | 47.2(t) | |
| 13 | 121.5(d) | 121.2(d) | |
| 14 | 136.8(s) | 137.8(s) | |
| 15 | 38.9(t) | 38.8(t) | |
| 16 | 25.9(t) | 25.7(t) | |
| 17 | 123.6(d) | 123.5(d) | |
| 18 | 134.5(s) | 134.3(s) | |
| 19 | 39.1(t) | 39.1(t) | |
| 20 | 26.2(t) | 26.1(t) | |
| 21 | 124.1(d) | 124.0(d) | |
| 22 | 130.5(s) | 130.4(s) | |

TABLE 7-continued $^{13}$C NMR Spectral Data of BU-4664L (1), Its Trimethyl Derivative (3) and Compound-1 (4) (100 MHz in DMSO-$d_6$)

| Carbon | 1 | 3 | 4 |
| --- | --- | --- | --- |
| 23-CH$_3$ | 16.1(q) | 16.0(q) | |
| 24-CH$_3$ | 15.7(q) | 15.6(q) | |
| 25-CH$_3$ | 17.4(q) | 17.3(q) | |
| 26-CH$_3$ | 25.4(q) | 25.3(q) | |
| 4-OCH$_3$ | | 56.4(q) | 56.5(q) |
| 7-OCH$_3$ | | 55.3(q) | 55.3(q) |
| 9-OCH$_3$ | | 56.6(q) | 56.3(q) |

$^a$The chemical shifts may be interchanged.
$^b$Multiplicity in off-resonance spectrum.

Figure 2:
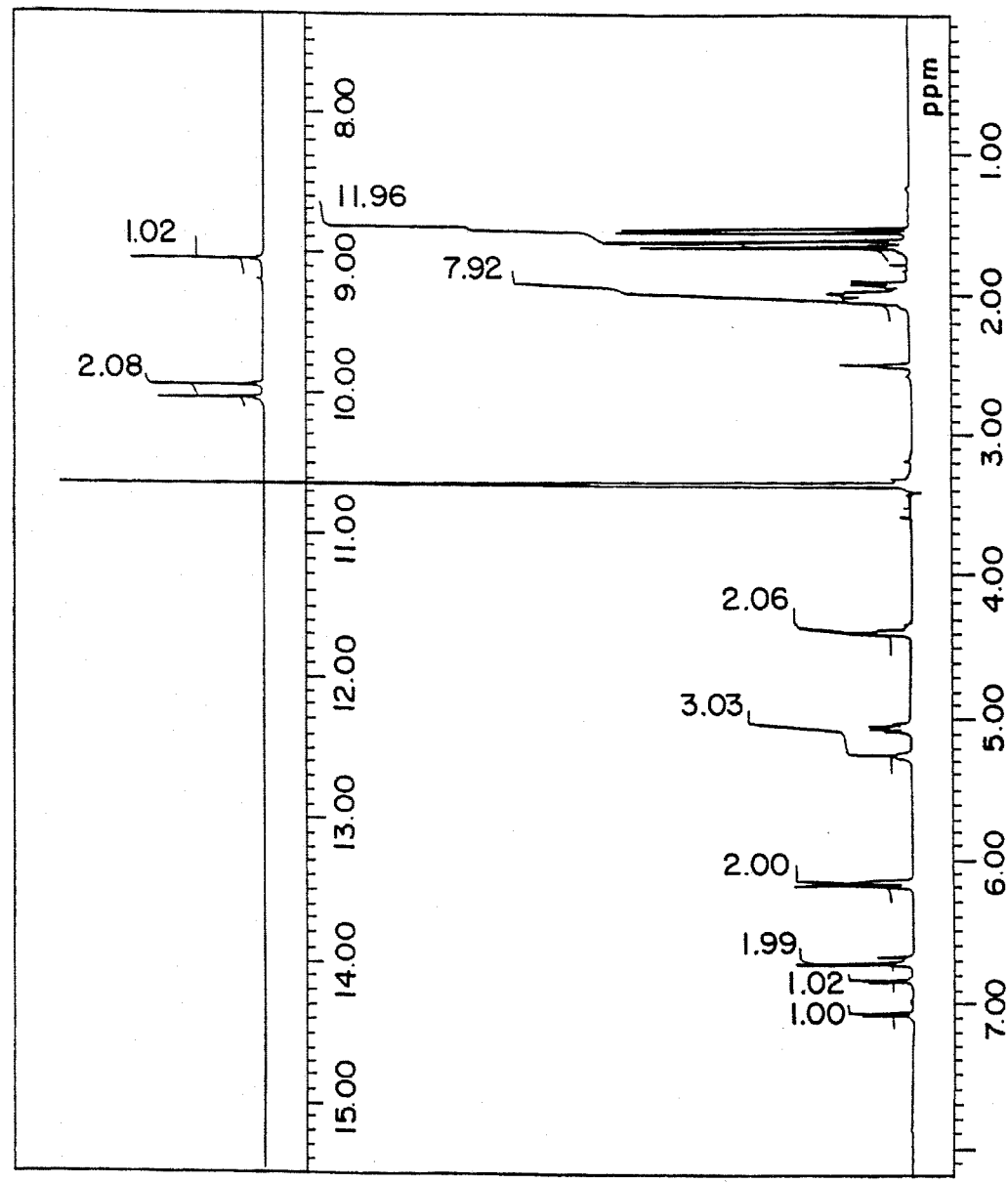
FIG. 2—Proton nuclear magnetic resonance ($^1$H-NMR) spectrum of compound BU-4664L (400 MHz, DMSO-$d_6$).
Figure 3:
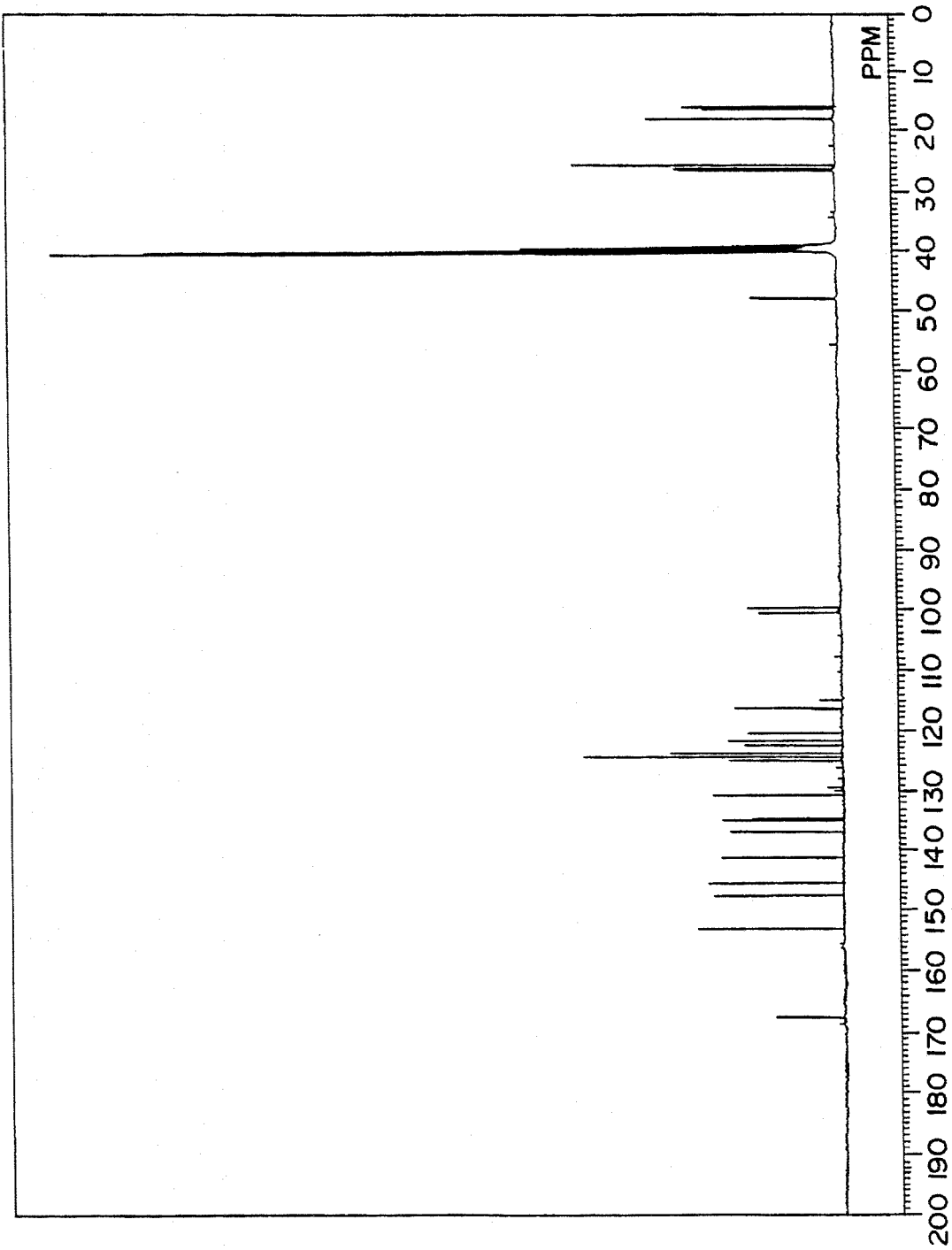
FIG. 3—$^{13}$C-NMR spectrum of compound BU-4664L (100 MHz, DMSO-$d_6$).

The UV spectrum exhibits absorption maxima at 211 and 292(sh) nm in methanol and 0.01N HCl-methanol and 208, 252(sh), 280(sh), 340(sh) and 553 nm in 0.01N NaOH-methanol. The IR spectrum (FIG. 1) shows absorption bonds at 3370, 2930, 1615, 1580, 1535, 1490, 1440, 1280, 1165 and 1150 cm$^{-1}$. The $^1$H-NMR spectrum (FIG. 2 and Table 6) of BU-4664L exhibits four methyl (δ 1.51, 1.54, 1.61 and 1.65, each s), five methylene (δ 1.91, 1.98, 1.97–2.03 (4H) and 4.39), three olefinic (δ 5.04, 5.06 and 5.25), five aromatic protons (δ 6.15, 6.17, 6.70, 6.83 and 7.06), one amido (δ 6.72) and three phenolic hydroxyl groups (δ 9,03, 9.94 and 10.03). The $^{13}$C-NMR spectrum (FIG. 3 and Table 7) shows 28 carbon signals which were assigned to four methyl, five methylene, eighteen sp$^2$ and one amido carbon.

Structural Determination

The UV spectrum of BU-4664L (1) showed the bathochromic shift in alkaline solution, suggesting the presence of phenolic hydroxyl groups in the molecule. The IR spectrum (FIG. 1) of 1 shows the presence of hydroxyl (3360 cm$^{-1}$), olefinic and/or aromatic (1610, 1590 and 1490 cm$^{-1}$) and amido groups (1535 cm$^{-1}$). The FAB-MS (positive) spectrum of 1 showed the pseudo-molecular ions at m/z 462 (M$^+$), 485(M+Na)$^+$ and 501 (M+K)$^+$ as well as a series of fragment ions at m/z 393 (M–C$_5$H$_9$)$^+$, 325(M–C$_{10}$H$_{17}$)$^+$, 258(M–C$_{15}$H$_{24}$)$^+$: base peak) and 69. These fragment ions indicated that 1 possessed a farnesyl residue (Maxwell, A. and D. Rampersad, "Prenylated 4-Hydroxybenzoic Acid Derivatives From *Piper saltuum*," *J. Nat. Prod.*, 51(2), 370–373, 1988; Maxwell, A. and D. Rampersad, "Novel Prenylated Hydroxybenzoic Acid Derivatives From *Piper saltuum*," *J. Nat. Prod.*, 52(3), 614–618, 1989) in the molecule. The molecular formula of 1 was established as C$_{28}$H$_{34}$N$_2$O$_4$ from the FAB-MS (positive, m/z 462(M$^+$) and negative, m/z 461(M–H)$^-$) and the microanalysis. Its $^1$H and $^{13}$C-NMR spectral data (FIGS. 2 and 3; Tables 6 and 7) revealed the presence of 1,2,3-trisubstituted (A ring) and 1,2,3,5-tetrasubstituted (B ring) benzene rings, three phenolic hydroxyl and one amido groups together with signals assignable to a farnesyl residue (Maxwell, A. and D. Rampersad, "Prenylated 4-Hydroxybenzoic Acid Derivatives From *Piper saltuum*," *J. Nat. Prod.*, 51(2), 370–373, 1988; Maxwell, A. and D. Rampersad, "Novel Prenylated Hydroxybenzoic Acid Derivatives From *Piper saltuum*," *J. Nat. Prod.* 52(3), 614–618, 1989). The farnesyl residue was linked to a nitrogen atom in view of the NMR chemical shifts of its terminal methylene [δ$_H$ 4.39 (d, J=6.0 Hz ) and δ$_c$ 47.4(t)] (Seto, et al., "Novel Quinoxaline Derivative (BK97), its Use as Anticancer agent, and its Manufacture with Streptomyces," Japan Kokai 3-232887 (1991) Oct. 16, 1991; Shinya, et al., "The Structure of Benthocyanin A. A New Free Radical Scavenger of Microbial Origin," *Tetrahedron Lett.*, 32 (7), 943, 1991). The stereochemistry within the farnesyl residue was established as all (E) based on the $^{13}$C-NMR chemical shifts (Maxwell, A. and D. Rampersad, "Prenylated 4-Hydroxybenzoic Acid Derivatives From *Piper saltuum*," *J. Nat. Prod.*, 51(2), 370–373, 1988; Maxwell, A. and D. Rampersad, "Novel Prenylated Hydroxybenzoic Acid Derivatives From *Piper saltuum*," *J. Nat. Prod.*, 52(3), 614–618, 1989) of the vinyl methyl groups (23-CH$_3$: δ 16.1, 24-CH$_3$: δ 15.7 and 25-CH$_3$: δ 17.4) except for the 26-CH$_3$ group (δ 25.3) resonated at lower field. In the $^1$H-NMR spectrum, the remaining portion of the structure (C$_{13}$H$_9$N$_2$O$_4$) showed three contiguous protons (δ 6,89, 7.05 and 7.22) and a pair of meta coupling protons (δ 6.46 and 6.50, d, J=2.6 Hz) due to A and B benzene rings, respectively, together with one amido (δ 6.72) and three phenolic hydroxyl groups (δ 9.03, 9.94 and 10.03). The $^{13}$C-NMR spectral data (FIG. 3 and Table 7) confirmed the presence of a farnesyl residue (Maxwell, A. and D. Rampersad, "Prenylated 4-Hydroxybenzoic Acid Derivatives From *Piper saltuum*," *J. Nat. Prod.*, 51(2), 370–373, 1988; Maxwell, A. and D. Rampersad, "Novel Prenylated Hydroxybenzoic Acid Derivatives From *Piper saltuum*," *J. Nat. Prod.*, 52(3), 614–618, 1989) and indicated the presence of twelve carbons including three oxygen bearing aromatic carbons (δ 145.4, 147.5 and 152.9) and one amido carbon (δ 167.5) due to the remaining portion.

Acetylation of 1 in pyridine gave the triacetate (2) which showed a pseudomolecular ion at m/z 589(M+H)$^+$ in the FAB-MS spectrum. The $^1$H NMR spectrum of 2 revealed the presence of three acetyl groups (δ 2.23, 2.37 and 2.39) and showed downfield shifts for meta coupling protons (δ 6.86 and 7.08) of B ring and one of three contiguous protons (δ 7.50) when compared with those of 1 (6-H, δ 6.15; 8-H, δ 6.17 and 3-H, δ 6.70, respectively), supporting that three phenolic hydroxyl groups locate at ortho position of these protons in 1. Methylation of 1 with diazomethane in benzene-methanol mixture yielded the trimethyl derivative which showed the molecular ion at m/z 504 (M$^+$) together with a fragment ion at m/z 300 (M$^+$-farnesyl, base peak) in the EI-MS spectrum. The $^1$H NMR spectrum of 3 (Table 6) is closely related to that of 1 except for three methoxy groups (δ 3.68, 3.84 and 3.88). In the $^{13}$C-$^1$H long range COSY experiment of 3, the correlations were observed between a proton (H-1, δ 7.22) of A ring and amido carbon (C-11, δ 167.1), between an amido proton (10-NH, δ6.83) and a methoxy bearing carbon (C-9, δ150.0) of B ring and between the terminal methylene proton (H-12, δ4.39) of the farnesyl residue and an aromatic carbon (C-4a, δ 134.4), respectively. The NOE experiment of 3 showed a correlation between the terminal methylene proton (H-12, δ 4.39) and a proton (H-6, δ 6.14) of B ring. Methanolysis of 3 by reflux with 1.5N HCl-MeOH gave compound-I (4) which showed the molecular ion at m/z 300 (M$^+$) and a fragment ion at m/z 150 [M$^+$-C$_8$H$_9$NO$_2$, base peak]. The molecular formula of 4 was found to be C$_{16}$H$_{16}$N$_2$O$_4$ by the HREI-MS (M$^+$, found m/z 300. 1110, calcd m/z 300. 1136). The $^1$H- and $^{13}$C-NMR spectra of 4 (Tables 6 and 7) indicated that 4 possessed a secondary amine (5-NH, δ 9.77) in place of a farnesyl residue in the molecule. In the $^{13}$-$^1$H long range COSY experiment of 4, the long range correlations were observed between an amino proton (5-NH, δ 9.77) and four aromatic carbons (C-5a, δ 126.8; C-6, δ 98.2; C-9a, δ 121.3; C-11a, δ 122.5), and between an amido proton (10-NH, δ 6.86) and three aromatic carbons (C-5a, δ 126.8; C-9, δ 149.7; C-11a, δ 122.5), indicating the presence of a seven-membered ring including an amine group and an amido group in the molecule of 4. According to these data, the structure of 4 was elucidated to be 4,7,9-trihydroxy-dibenzo[b,e][1,4]diazepin- 11-one. Thus, the structure of BU-4664L (1) was determined as 5-farnesyl- 4,7,9-trihydroxy dibenzo[b,e][1,4]diazepin-11-one. These structures are as follows:

Structures of BU-4664L, its derivatives and compound-I

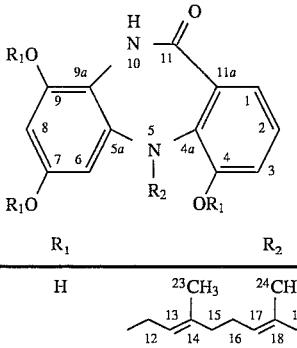

| | $R_1$ | $R_2$ |
|---|---|---|
| BU-4664L (1) | H | farnesyl chain (positions 12-26 with methyls at 23, 24, 25) |
| Triacetyl BU-4664L (2) | COCH$_3$ | . |
| Trimethyl BU-4664L (3) | CH$_3$ | . |
| Compound-I (4) | CH$_3$ | H |

5-Lipoxygenase Inhibitory Activity

The 5-lipoxygenase (5-LPO) inhibitory effect (Hook, et al., "Identification of the Inhibitory Activity of Carbazomycins B and C Against 5-Lipoxygenase, A New Activity for These Compounds," *J. antibiotics*, 43, 1347–1348, 1990) was determined by measuring the amount of 5-hydroxyeicosatetraenoic acid (5-HETE) produced in a cell-free extract of rat basophilic leukemia cells (RBL-1 cells, ATCC CRL 1378) in the presence of a test sample, arachidonic acid, adenosine triphosphate, CaCl$_2$ and glutathione. The 5-HETE produced was separated by high performance liquid chromatography (HPLC, Rainin Dynamax C18, 0.46 i.d.×5 cm) with an HPLC solvent of 82% MeOH-18% 29.2 mM lithium acetate buffer (pH 6.3) at a flow rate of 1 ml/minute. The concentration of 5-HETE was spectrophotometrically measured at 230 nm with a Gilson 115 UV detector and a Hewlett Packard 3396a integrator.

BU-4664L was discovered in the fermentation broth of *Micromonospora* sp. strain No. M990-6. The IC$_{50}$ values of Bu-4664L and its derivatives for rat 5-LPO inhibitory activity were determined and described in Table 8. Bu-4664L exhibited good 5-LPO inhibitory activity (IC$_{50}$: 1.7 µM/ml), but its triacetyl and trimethyl derivatives protected phenolic hydroxyl groups with an acetyl or a methyl group, respectively, seemed to be devoid of 5-LPO inhibitory activity.

TABLE 8

| 5-Lipoxygenase Inhibitory Activity | |
|---|---|
| Compound | IC$_{50}$ (in µmoler) |
| BU-4664L | 1.7 |
| Triacetyl Bu-4664L | >34.0 |
| Trimethyl BU-4664L | >39.6 |

Antitumor Activity

In Vitro Cytoxicity. B16–F10 (murine melanoma) and Moser (human colorectal carcinoma) were grown in Eagle's minimum essential medium (Nissui) supplement with fetal calf serum (FCS, 10%) and kanamycin (60 µg/ml), HCT-116 (human colon carcinoma) cells were grown in McCoy's 5A Medium (Gibco) supplemented with FCS (10%), penicillin (100 u/ml) and streptomycin (100 µg/ml), and K562 (human myelogenous leukemia) were in RPM 11640 medium supplemented with FCS (10%), penicillin (100 u/ml) and streptomycin (100 µg/ml) at 37° C. under humidified atmosphere in a CO$_2$ incubator. The exponentially growing B16–F10, Moser, K562 and HCT-116 cells were harvested, counted and suspended in the culture media at 1.5×10$^4$, 6×10$^4$, 3×10$^4$ and 8×10$^4$ cells/ml, respectively. The test materials were planted into the wells of 96 or 24-well tissue culture plate and for 72 hours. The cytotoxic activities were colorimetrically determined at 540 nm after staining viable cells with neutral red solution.

Bu-4664L (1) inhibited growth of the murine and human tumor cell lines with the IC$_{50}$ values of 2.6 µg/ml (vs HCT-116) and 1.1–18 µg/ml (vs K562, B16–F10 and Moser), respectively (Table 9). the derivatives (2) and (3) exhibited weaker cytotoxicity against B16–F10 and HCT-116 cells than those of BU-4664L.

TABLE 9

| In Vitro Cytotoxicity | | | | |
|---|---|---|---|---|
| | IC$_{50}$ (µg/ml) | | | |
| Compound | B16-F10 | HCT-116 | Moser | K562 |
| BU-4664L | 1.9 | 2.6 | 18 | 1.1 |
| Triacetyl Bu-4664L | 2.4 | 4.4 | NT | NT |
| Trimethyl BU-4664L | 21.0 | 12.5 | NT | NT |

NT: Not tested
B16-F10 (murine melanoma)
HCT-116 (human colon carcinoma)
Moser (human colorectal carcinoma)
K562 (human myelogenous leukemia)

In Vivo Antitumor Activity

B16 melanoma was intraperitoneally (ip) inoculated with 0.5 ml of 10% brei per male BDF$_1$ mouse, and P388 leukemia intraperitoneally inoculated with 10$^6$ cells per female CDF$_1$ mouse. The test materials were intraperitoneally administered to the tumor-bearing mice by the following treatment schedules: once daily on days 1 to 3 (Q1D×3), once a day on days 1, 4, and 7 (Q3D×3) and once a day on days 1, 5 and 9 (Q4D×3).

The in vivo antitumor activity was determined in tumor-bearing mice. BU-4664L demonstrated significant prolongation of the survival time of mice inoculated with P388 (Table 10) and B16 melanoma (Table 11). BU-4664L exhibited good T/C values against P388 leukemia, but was weaker than Mitomycin C against B16 melanoma in terms of minimum effective dose.

TABLE 10

Antitumor Activity of BU-4664L Against P388 Leukemia (ip)

| Compound | Dose mg/kg/day) | Treatment Schedule (ip) | MST* (day) | T/C** (%) | Avg Weight change on day 4 (g) |
|---|---|---|---|---|---|
| BU-4664L | 30 | Q1D × 3 | 16.0 | 160 | −1.1 |
|  | 10 | " | 15.0 | 150 | −1.8 |
|  | 3 | " | 13.0 | 130 | 0.0 |
|  | 1 | " | 11.0 | 110 | +0.5 |
|  | 0.3 | " | 12.0 | 120 | +0.5 |
| BU-4664L | 30 | Q3D × 3 | 12.5 | 152 | −2.3 |
|  | 10 | " | 16.2 | 162 | +0.5 |
|  | 3 | " | 15.2 | 152 | +1.3 |
|  | 1 | " | 11.9 | 119 | +0.3 |
| Mitomycin C | 3 | Q1D × 3 | 21.0 | 200 | −1.5 |
|  | 1 | " | 16.0 | 152 | 0.0 |
|  | 0.3 | " | 12.5 | 119 | +0.3 |
| Vehicle | — |  | 10.5 | — | +0.1 |

*Median survival time
**% T/C: MST treated/MST control X100 (criteria: % T/C ≧ 125 considered to be significantly active)

TABLE 11

Antitumor Activity of BU-4664L Against B16 Melanoma (ip)

| Compound | Dose mg/kg/day) | Treatment Schedule (ip) | MST* (day) | T/C (%) | Avg Weight change on day 5 (g) |
|---|---|---|---|---|---|
| BU-4664L | 30 | Q4D × 3 | 17.0 | 131 | −0.8 |
|  | 10 | " | 17.5 | 135 | +0.3 |
|  | 3 | " | 16.5 | 127 | +0.3 |
| Mitomycin C | 2 | Q4D × 3 | 26.7 | 204 | +0.3 |
|  | 1 | " | 22.5 | 173 | +0.5 |
|  | 0.5 | " | 16.0 | 123 | +0.8 |
| Vehicle | — | Q4D × 3 | 13.0 | — | 0.0 |

*Median survival time

EXAMPLE 3

Preparation of Derivatives of Compound BU-4664L

Acetylation

BU-4664L (20 rag) was stirred with acetic anhydride (1.0 ml) in anhydrous pyridine (1.5 ml) for 18 hours at room temperature. To the reaction mixture, EtOAc and water (20 ml each) were added and stirred for one hour. After washing with water (20 ml portions) twice, the organic layer was concentrated to give a yellow solid. The residue was purified by preparative TLC (SiO$_2$, CH$_2$Cl$_2$-MeOH 20:1) followed by Sephadex LH-20 chromatography using CH$_2$Cl$_2$-MeOH (4:6) as a developing solvent to give triacetate BU-4664L (2, 13 mg), m.p. >200° C. (dec.).

Methylation

To a solution of BU-4664L (32 mg) in a mixture of methanol (1 ml) and benzene (2 ml) was added trimethyl silyl diazomethane in n-hexane (0.8 ml) while stirring. After stirring for 15 hours at room temperature, the reaction mixture was evaporated in vacuo and the residue was purified by preparative TLC (SiO$_2$, CH$_2$Cl$_2$-MeOH 20:1) followed by Sephadex LH-20 chromatography using CH$_2$Cl$_2$-MeOH (4:6) as a developing solvent to yield trimethyl BU-4664L (3, 18 mg), m.p. >200° C. (dec.).

Preparation of Compound I (4)

A solution of trimethyl BU4664L (3, 15 mg) in 1.5 N HCl-MeOH (2 ml) was refluxed for 2 hours. To the reaction mixture, ethyl acetate (EtOAc) and water (20 ml each) were added and stirred for half an hour. After washing with water (20 ml portions) twice, the organic layer was evaporated in vacuo and the residue was recrystallized from a mixture of MeOH and CH$_2$Cl$_2$ to afford compound I (4, 5 mg) as yellow needles, m.p. >200° C. (dec.).

Other derivatives of Compound BU-4664L within the scope of Formula A can be made using appropriate reagents and conditions analogous to those described herein, or by other means using routine experimentation by one of ordinary skill in the art.

The invention has been described in detail with particular reference to preferred embodiments thereof, but it will be understood that variations and modifications can be effected within the spirit and scope of the invention.

We claim:

1. A compound of the formula

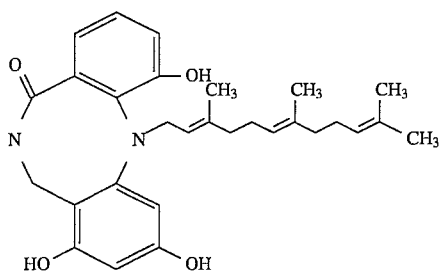
or a pharmaceutically acceptable salt thereof.
2. A pharmaceutical composition comprising a compound of the formula
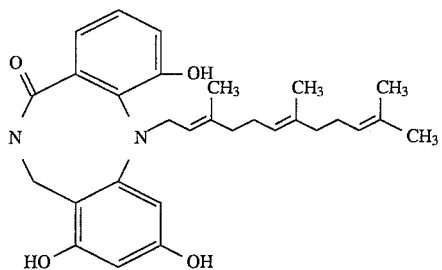
or a pharmaceutically acceptable salt thereof, together with a pharmaceutically acceptable carrier.
* * * * *